United States Patent
Abdel-Rahman et al.

(10) Patent No.: US 6,497,138 B1
(45) Date of Patent: Dec. 24, 2002

(54) MULTILAYERED GAS CHROMATOGRAPH

(75) Inventors: Mahmoud Farid Abdel-Rahman, Newark, DE (US); Carl A. Myerholtz, Cupertino, CA (US)

(73) Assignee: Agilent Technologies, Inc.,, Palo Alto, CA (US)

( * ) Notice: Subject to any disclaimer, the term of this patent is extended or adjusted under 35 U.S.C. 154(b) by 0 days.

(21) Appl. No.: 09/691,601

(22) Filed: Oct. 18, 2000

(51) Int. Cl.[7] ............. G01N 30/04; B01D 53/02
(52) U.S. Cl. ........ 73/23.42; 73/23.26; 73/23.39; 73/23.35; 96/104; 96/105; 95/86
(58) Field of Search ............ 73/23.25, 23.26, 73/23.35, 23.39, 23.4, 23.41, 23.42; 96/104, 105; 95/86

(56) References Cited

U.S. PATENT DOCUMENTS

| | | | |
|---|---|---|---|
| 3,856,681 A | | 12/1974 | Huber |
| 4,180,309 A | * | 12/1979 | Paul ................... 95/11 |
| 4,883,504 A | * | 11/1989 | Gerstel ................ 95/8 |
| 4,935,040 A | * | 6/1990 | Goedert ............... 96/104 |
| 5,014,541 A | * | 5/1991 | Sides et al. .......... 73/23.41 |
| 5,567,868 A | * | 10/1996 | Craig et al. .......... 73/24.42 |
| 5,652,398 A | * | 7/1997 | Johnson .............. 73/863.71 |
| 5,933,357 A | * | 8/1999 | Tipler ................. 95/88 |
| 5,983,703 A | * | 11/1999 | Wylie et al. ......... 73/23.42 |
| 6,068,684 A | * | 5/2000 | Overton .............. 96/104 |
| 6,257,047 B1 | * | 7/2001 | Grob et al. .......... 73/23.42 |
| 6,306,200 B1 | * | 10/2001 | Yu .................... 96/102 |

FOREIGN PATENT DOCUMENTS

| | | |
|---|---|---|
| EP | 0 654 667 A1 | 5/1995 |
| EP | 0 806 661 A1 | 11/1997 |
| JP | 56-21063 | 2/1981 |
| JP | 61-9005 | 5/1986 |

* cited by examiner

Primary Examiner—Hezron Williams
Assistant Examiner—Michael Cygan

(57) ABSTRACT

The present disclosure relates to a gas chromatograph having a plurality of layers or channels. The chromatograph typically comprises an inlet that receives a sample to be analyzed, a column disposed in each of the plurality of chromatograph layers, each column being in fluid communication with and downstream from the inlet and having a stationary phase coating its inner surfaces, and a detector in fluid communication with and downstream from at least one of the columns. In a preferred arrangement, the chromatograph includes a pre-column disposed in each of the chromatograph layers upstream of the columns, each pre-column being in fluid communication with the inlet and having a stationary phase coating its inner surfaces.

26 Claims, 8 Drawing Sheets

US 6,497,138 B1

MULTILAYERED GAS CHROMATOGRAPH

FIELD OF THE INVENTION

The present disclosure generally relates to a gas chromatograph. More particularly, the disclosure relates to a multilayered gas chromatograph with which sample analyses can be conducted quickly with minimal down time between analysis cycles.

BACKGROUND OF THE INVENTION

Gas chromatography is a field concerned with analyzing samples of interest, which may include one or more analytes, to qualitatively determine the identity of the analytes as well as to quantitatively determine the concentration of each of the analytes in the sample. Gas chromatography is extremely sensitive and therefore is normally used where very precise analysis of a sample is required. The analysis can comprise the identification of the various individual analytes, or comparison of the entire sample response (e.g., chromatogram) to previously analyzed samples for the purpose of classifying the sample.

Gas chromatography typically involves separation of the analytes of a sample material through use of a gas chromatograph. Normally, gas chromatographs comprise an inlet in which the sample is injected, a column in which the analytes are separated, and a detector in which the various analytes are detected and, if desired, quantitatively evaluated. The column usually is made from fused silica that is formed into a narrow, elongated tube. By way of example, the chromatograph column can have an inner diameter on the order of approximately 50 to 530 microns ($\mu$m), and a length of approximately 1 to 30 meters. To decrease the size of the chromatograph apparatus, the column normally is arranged in a coiled configuration. By way of example, the coil can have a diameter of approximately 8 inches (in) such that the column can be packaged, for instance, in a cubic foot of space.

The interior walls of the gas chromatograph column are coated with a material commonly referred to as a stationary phase. The stationary phase retains the various analytes of the injected sample and, through the application of heat, releases the analytes so that they are received by the detector separated in time. Through knowledge of the temperature of the column and the duration of time that passes between injection and detection, the individual analytes passing through the detector can be identified.

As is known in the art, heavier compounds require more heat and/or more time to elute from the column than do lighter compounds. For instance, at a relatively low temperature (e.g., at 100° C.), the lighter analytes may elute from the column stationary phase after only a few seconds while the heavier analytes may require many minutes or even hours to separate. Therefore, it can be appreciated that the greater the heat, the faster the heavier analytes can be eluted from the column. Where the sample is complex, however, for instance having several light and heavy components, high temperatures (e.g., 300° C.) cause the lighter analytes to immediately elute such that many different analytes arrive at the detector simultaneously. This simultaneous arrival complicates the analysis of the sample analytes in that, where the detector is non-selective, the detector cannot distinguish the various analytes from each other. To avoid this problem, gas chromatographs are often heated in a programmed, air-bath oven which increases the temperature of the column at a steady rate (e.g., 20° C./minute). By heating the column in this manner, the low temperatures needed for adequate separation of the lighter analytes are provided, as well as the higher temperatures needed to elute the heavier analytes from the column.

Although adequately functional for most sample analysis situations, conventional gas chromatographs present several drawbacks. First, a cool down period normally is needed in between analysis cycles to reduce the temperature of the column from the final temperature to the initial temperature. By way of example, this cool down can require approximately 15 minutes or more. Although not an exceedingly long period of time, this duration is substantial, especially where the samples are being analyzed with "fast" chromatography which often only requires a few minutes. In addition to cool down time, time is wasted in permitting the system to achieve equilibrium. As is known in the art, if thermal equilibrium is not achieved prior to conducting a sample analysis, substantial fluctuation in analyte retention times can occur. Furthermore, column bleed fluctuations that occur during over temperature programming can increase the chromatogram baseline noise and/or drift that can mask analyte peaks.

From the foregoing, it can be appreciated that it would be desirable to have a gas chromatograph with which sample analyses can be conducted quickly with minimal down time between analysis cycles.

SUMMARY OF THE INVENTION

The present disclosure relates to a gas chromatograph having a plurality of layers or channels. The chromatograph typically comprises an inlet that receives a sample to be analyzed, a column disposed in each of the plurality of chromatograph layers, each column being in fluid communication with and downstream from the inlet and having a stationary phase coating its inner surfaces, and a detector in fluid communication with and downstream from at least one of the columns. In a preferred arrangement, the chromatograph includes a pre-column disposed in each of the chromatograph layers upstream of the columns, each pre-column being in fluid communication with the inlet and having a stationary phase coating its inner surfaces.

The features and advantages of the invention will become apparent upon reading the following specification, when taken in conjunction with the accompanying drawings.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

Figure 1:
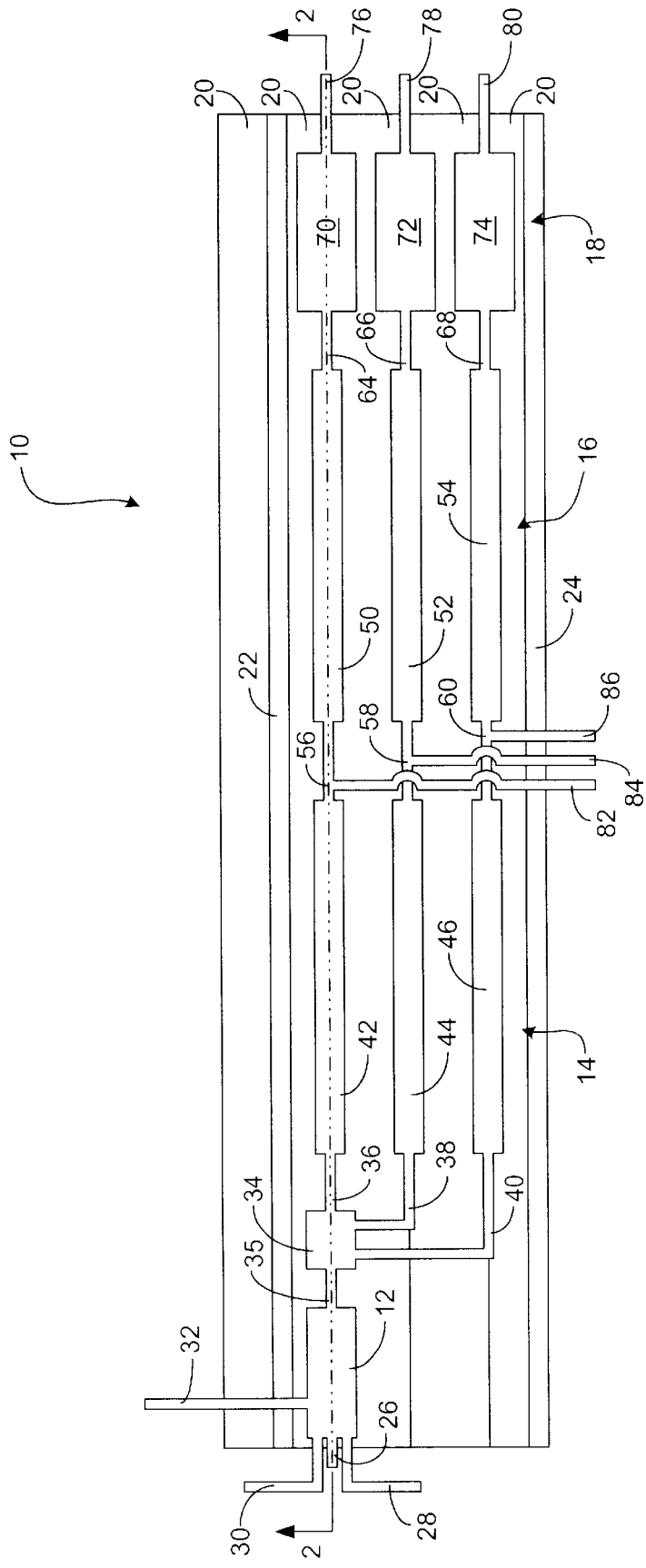
FIG. 1 is a schematic side view of a first gas chromatograph of the present invention.
Figure 2:
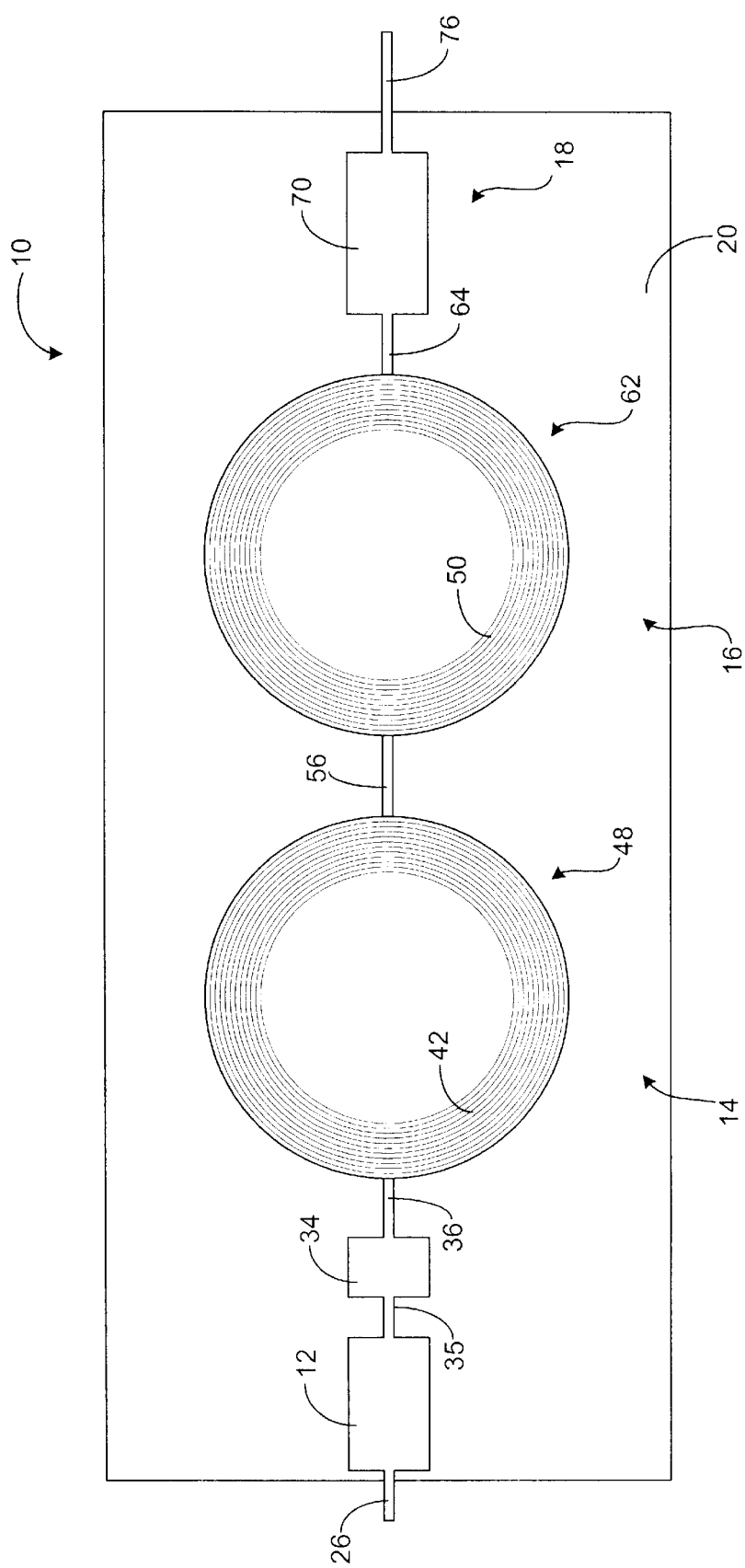
FIG. 2 is a schematic top view of the gas chromatograph of FIG. 1, taken along line 2—2.

Referring now in more detail to the drawings, in which like numerals indicate corresponding parts throughout the several views, FIGS. 1 and 2 illustrate a first gas chromatograph 10 of the present invention. As will be understood by persons having ordinary skill in the art, these figures primarily illustrate the column configurations of the gas chromatograph 10 and therefore do not necessarily illustrate every component necessary to operation of the system.

With reference to FIG. 1, the gas chromatograph 10 generally comprises an inlet 12, a plurality of pre-columns 14, a plurality of main columns 16, and a plurality of detectors 18. As indicated in FIG. 1, the various pre-columns 14, main columns 16, and detectors 18 are arranged in different layers or channels such that the gas chromatograph 10 has a multi-layer or multi-channel configuration. By way of example, three such layers can be provided. In such an arrangement, the chromatograph 10 can have a height dimension of approximately 1 to 3 inches, a length dimension of approximately 4 to 12 inches, and a width dimension (FIG. 2) of approximately 2 to 6 inches. As illustrated in FIG. 1, each layer of the gas chromatograph 10 is formed with various insulation layers 20 that, by way of example, can be constructed of calcium silicate. In the arrangement shown in FIG. 1, five insulation layers 20 are provided. Preferred for the construction of the insulation layers is the Super Firetemp L material available from Pabco.

Disposed between the top two insulation layers 20 of the chromatograph 10 is a first heat source 22. In addition, a second heat source 24 is positioned adjacent the fifth insulation layer 20. With this configuration, each of the various layers of the gas chromatograph 10 are positioned intermediate the two heat sources 22 and 24. By way of example, the heat sources 22, 24 can each comprise a heat plate constructed of a metal material such as stainless steel and provided with a thick film heater that is deposited on the plate surface. Suitable thick film heaters are available from Watlow Industries. As will be understood from the discussion that follows, the heat sources 22 and 24 heat the inlet 12, pre-columns 14, main columns 16, and detectors 18 of the gas chromatograph 10. More particularly, the first and second heat sources 22 and 24 provide heat to the gas chromatograph 10 at different temperatures such that a thermal gradient is established across the chromatograph layers. With such a thermal gradient, each layer of the gas chromatograph 10 is positioned at a different isotherm and therefore will have a different temperature when thermal equilibrium is reached.

Typically, the inlet 12 is formed as a split/splitless inlet of conventional design. The inlet 12 includes a septum 26 in which a sample to be analyzed can be injected into the chromatograph 10. As is further illustrated in FIG. 1, the inlet 12 normally is in fluid communication with an inlet supply line 28 and first and second inlet vents 30 and 32. As is discussed below, the inlet supply line 28 delivers carrier gas to the inlet 12. Normally, the first inlet vent 30 is connected to the septum 26 of the inlet 12, while the second inlet vent 32 is connected to the main body of the inlet 12. It is to be understood that alternative inlets or other sample introduction means can be used, if desired.

Disposed between the inlet 12 and the pre-columns 14 is a splitter 34. As indicated in FIG. 1, the splitter 34 is in fluid communication with the inlet 12 via a splitter supply line 35. In use, the splitter 34 receives carrier gas from the inlet 12 and divides the gas flow into three, normally equal, flows of carrier gas. Preferably, each chromatograph level or channel receives the same volume of carrier gas flow. Due to the different temperatures and the viscosity changes of the carrier gas due to these different temperatures, the sizes of the columns may be varied to ensure equal flow to each of the columns. Each of the resulting flows is directed to first, second, and third pre-column supply lines 36, 38, and 40 which deliver the gas to the first, second, and third pre-columns 42, 44, and 46, respectively. Each pre-column 14 comprises a narrow, elongated tube having a stationary phase that coats its inner surfaces. With reference to FIG. 2, the pre-columns 14 comprise capillary-type columns or packed-typed columns and preferably are arranged in coils 48 having a plurality of circular turns. The pre-column coils 48 can optionally be enclosed in a metal envelope (not shown) to help equalize the temperature across the coils. By way of example, coils 48 of capillary-type columns can have a diameter of approximately 3 inches and can comprise approximately 1 to 30 turns. By further way of example, the pre-columns 14 can have inner diameters of approximately 50 to 530 $\mu$m. As for packed-type columns, the pre-columns 14 can have inner diameters of approximately 2 to 3 mm.

Downstream from the pre-columns 14 are the main columns 16. As indicated in FIG. 1, the gas chromatograph 10 can comprise a first, second, and third main columns 50, 52, and 54. Like the pre-columns 14, the main columns 16 are provided with a stationary phase that coats the inner surfaces of the columns. The various pre-columns 14 are connected to these columns 16 with first, second, and third column supply lines 56, 58, and 60. Accordingly, in use, carrier gas can travel through each of the pre-columns 14, through each of the column supply lines 56–60, and into the various main columns 16. With reference to FIG. 2, each of the main columns 16 normally also is arranged as a capillary-type or packed-type column arranged in a coil 62 that comprises a plurality of circular turns. Like the pre-column coils 48, the main column coils 62 can be enclosed in a thin metal envelope (not shown) if desired to help equalize the temperatures across the coils. By way of example, for capillary-type columns, each of the coils 62 can be approximately three inches in diameter and can comprise approximately 4 to 120 turns. By further way of example, each main column 16 has an inner diameter of approximately 50 to 530 $\mu$m. For packed-type columns, each column 16 can have an inner diameter of approximately 2 to 3 mm.

After the carrier gas (and sample gas if applicable) leaves the main columns 16, it enters first, second, and third detector supply lines 64, 66, and 68, which carry the gas to the first, second, and third detectors 70, 72, and 74, respectively. It is in each of these detectors 18 that the various sample analytes are identified and, if desired, quantified. The carrier gas flows through the detectors 18 and is vented from the detectors with first, second, and third detector vents 76, 78, and 80, respectively.

With further reference to FIG. 1, the gas chromatograph 10 normally additionally comprises first, second, and third purge lines 82–86. As indicated in FIG. 1, the first, second, and third purge lines 82–86 are connected in fluid communication with the first, second, and third column supply lines 56–60, respectively. As is discussed below in greater detail, these purge lines 82–86 are used to flush the pre-columns 14, splitter 34, and inlet 12 after the sample gas has been delivered to the main columns 16.

Figure 3:
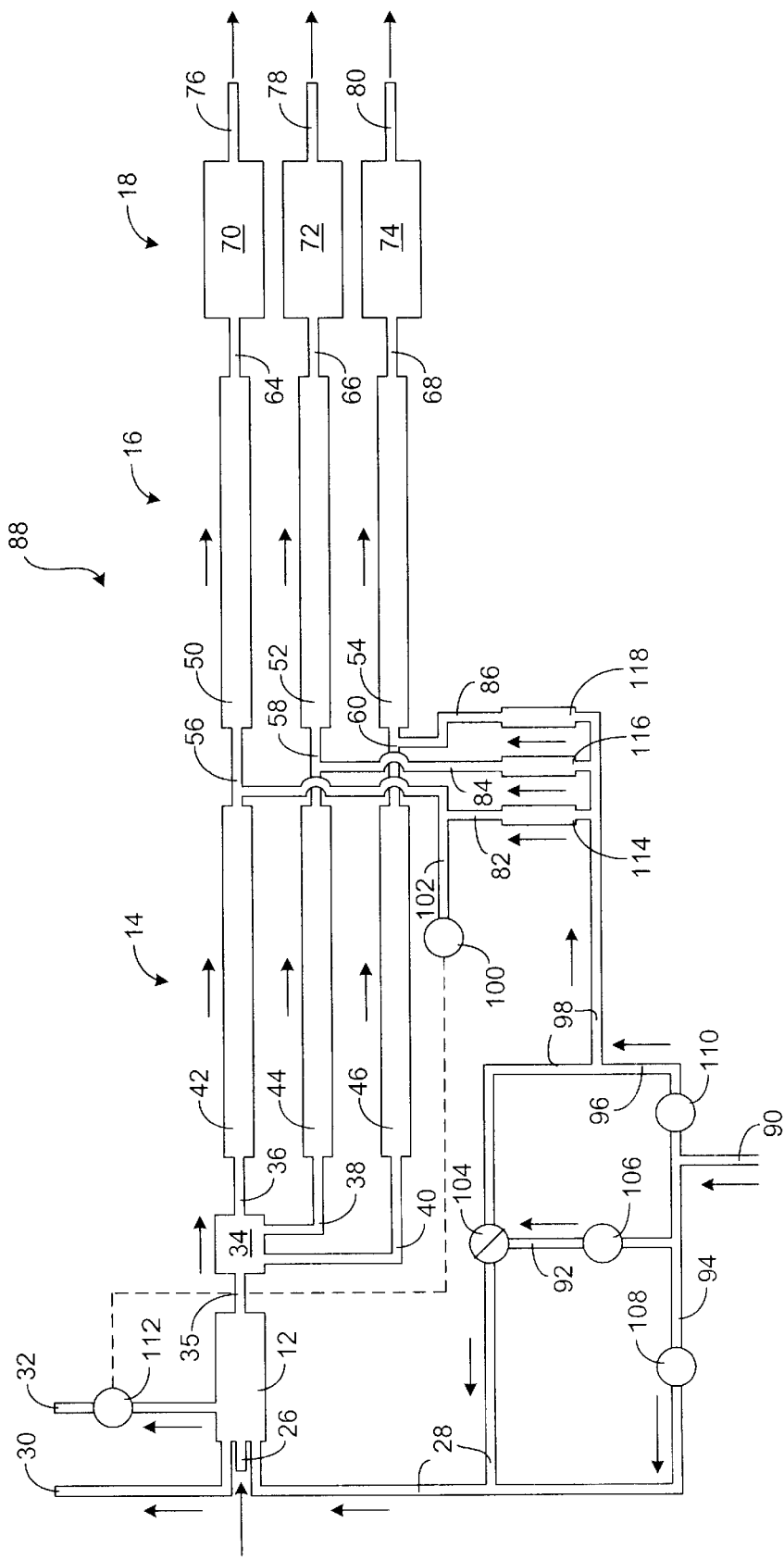
FIG. 3 is a schematic diagram of a pneumatic system of the gas chromatograph of FIG. 1, shown in a first mode of operation.
Figure 4:
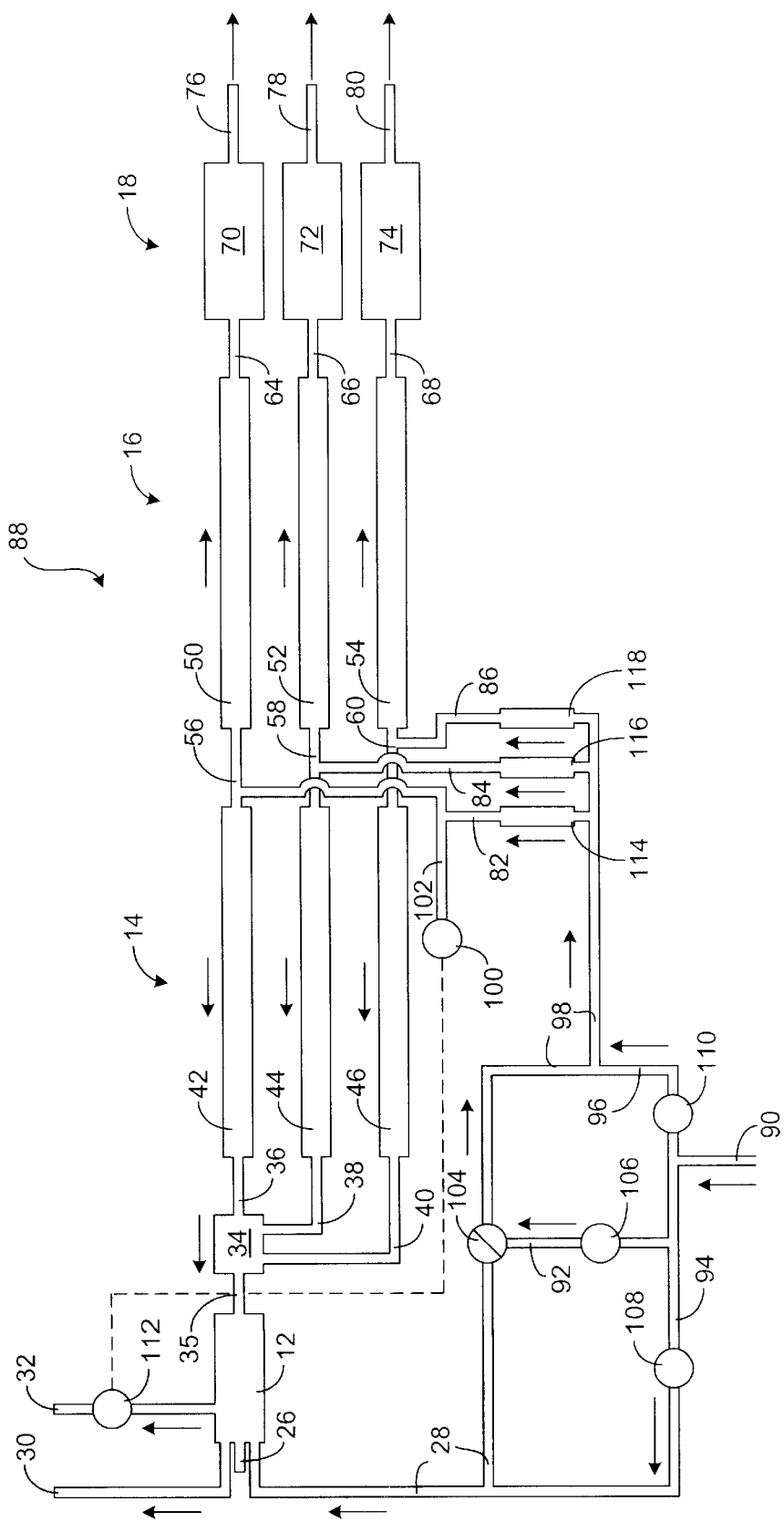
FIG. 4 is a schematic diagram of the pneumatic system of FIG. 3, shown in a second mode of operation.

FIGS. 3 and 4 illustrate a pneumatic system 88 used in the gas chromatograph 10. Although a particular routing arrangement is depicted in these figures, it is to be understood that modifications to this routing scheme is within the skill of persons having ordinary skill in the art. With reference first to FIG. 3, which illustrates a main column loading mode, the pneumatic system 88 comprises a system supply line 90 that is in fluid communication with the inlet supply line 28 via a first branch line 92. The system supply line 90 is also in fluid communication with a second branch line 94 and a third branch line 96. The pneumatic system 88 further includes a purge supply line 98 that is in fluid communication with the third branch line 96. The purge supply line 98 is also in fluid communication with each of the purge lines 82–86. Further illustrated in FIG. 3 is a pressure sensor 100 that is in fluid communication with a sensor line 102. The sensor line 102 is in fluid communication with the first purge line 82 and, therefore, also with the first column supply line 56.

With further reference to FIG. 3, disposed between the first branch line 92 and the inlet supply line 28 is a valve 104 with which the flow of carrier gas to the inlet supply line 28 can be enabled or interrupted. By way of example, the valve 104 comprises a two-way valve which either opens the flow of carrier gas to the inlet supply line 28 or to the purge supply line 98. Upstream from the valve 104 along the first branch line 92 is a flow controller 106. Similarly, flow controllers 108 and 110 can be disposed along the second and third branch lines 94 and 96, respectively. Typically, each flow controller 106–110 comprises a pressure sensor and a valve. Accordingly, the flow controllers 106–110 can sense the pressure of the flow traveling through the respective branch lines 92–96 and adjust the flow in response to the sensed pressures.

In addition to the aforementioned valves and flow controllers, the pneumatic system 88 typically further comprises a valve 112 that is disposed along the second inlet vent 32. As indicated with a dashed line in FIG. 3, the valve 112 is controlled relative to the pressure sensor 100. In a preferred arrangement, a control system (not shown) monitors the pressure sensed by the pressure sensor 100 and adjusts the valve 112 to control the pressure within the pre-columns 14 and main columns 16. In addition to valve 112, the pneumatic system 88 further typically comprises first, second, and third flow restricters 114, 116, and 118 that are disposed along purge lines 82–86, respectively. As is discussed below, the flow restricters 114–118 can be used to restrict the flow of carrier gas through the purge lines 82–86.

The primary components of the first gas chromatograph 10 having been described above, operation of the chromatograph 10 will now be discussed. With reference first to FIG. 1, the system is initiated by allowing the heat sources 22 and 24 to arrive at the desired temperatures. In a preferred arrangement, the first heat source 22 is heated to a relatively high temperature, e.g., 350° C., and the second heat source 24 is heated to a relatively lower temperature, e.g., 50° C. Heat is transferred from these sources 22, 24 through the various layers of the gas chromatograph 10 such that a temperature gradient is formed across the gas chromatograph from the first heat source 22 to the second heat source 24. By way of example, the first or top layer can achieve a temperature of approximately 300° C., the second or middle layer can achieve a temperature of approximately 200° C., and the third or bottom layer can achieve a temperature of approximately 100° C.

Once the gas chromatograph 10 has reached equilibrium and the desired heat gradient has been obtained, the chromatograph 10 can be used to analyze sample materials. Normally, a small sample of material is injected into the inlet 12 through the inlet septum 26. By way of example, the sample can be in liquid form and can have a volume of approximately 0.1 to 10 microliters. Upon entering the inlet 12, the sample is vaporized into a gas due to the inlet's proximity to the first heat source 22. As is known in the art, the carrier gas supplied to the inlet supply line 28 carries the sample gas through the chromatograph 10. By way of example, the carrier gas can comprise a substantially inert gas such as helium. This carrier gas can be supplied to the inlet 12 at a head pressure of approximately 1 to 50 pounds per square inch (psi). Due to the limited sample capacity of the column, part of the sample injected into the inlet 12 may be vented from the chromatograph 10 through the second inlet vent 32.

The sample gas is carried by the carrier gas from the inlet 12 to the splitter 34 which divides the flow into three, normally equal, flows that are directed along the pre-column supply lines 36–40. Typically, the flow delivered to the splitter 34 is controlled through a combination of the flow controller 106 and the valve 112. As discussed above, the pressure through the first layer (i.e., the first pre-column 42 and the first main column 50) is monitored with the pressure sensor 100. Accordingly, where the pressure in the first layer, and therefore the other remaining layers, is not at the desired pressure, the flow through the second inlet vent 32 can be controlled such that, where the pressure is too great, more gas is vented from the chromatograph 10 and, where the pressure is too low, less gas is vented through the second inlet vent 32. Notably, the pressure in each layer or channel is controlled at a single channel. In such an arrangement, the control channel is the master channel and the other channels are slave channels. Although this arrangement is preferred, it will be understood that each channel could be separately controlled, if desired.

After the gas flow has been divided by the splitter 34, the gas enters the pre-columns 14. Once reaching the pre-columns 14, a portion of the sample gas is trapped by the stationary phase disposed on the inner surfaces of the pre-columns. A remaining portion of the sample gas is delivered via the column supply lines 56–60 to the main columns 16 and is trapped by the stationary phase disposed on the inner surfaces of these columns. The carrier gas, and any analytes that have eluted from the stationary phase of the columns 16, then flows through the detector supply lines 64–68 to the detectors 18. As is discussed below, the detectors 18 detect the presence of the various analytes as they arrive at the detectors. From the detectors 18, the carrier gas is vented from the gas chromatograph 10 through the detector vents 76–80.

With reference to FIG. 3, a portion of the carrier gas supplied by the system supply line 90 is diverted into the second and third branch lines 94 and 96. In the second branch line 94, the flow controller 108 is used to control the amount of carrier gas carried along this line. The flow through the second branch line is normally constant such that when the flow of carrier gas from the first branch line 92 to the inlet supply line 28 is terminated, a relatively small amount of carrier gas will still flow through the inlet supply line 28 to the inlet 12. This flow prevents contamination of the inlet septum 26. With regard to the third branch line 96, carrier gas similarly constantly flows through the flow controller 110 such that a relatively small amount of carrier gas flow is provided to each of the purge lines 82–86 even when the full supply of carrier gas to the purge supply line 98 from the first branch line 92 is terminated. This flow prevents contamination of the purge lines 82–86 by sample analytes.

After the sample gas reaches the main columns 16, the flow of carrier gas through the pre-columns 14 is reversed such that the first half of the gas chromatograph 10 operates in reverse to that shown in FIG. 3. Normally, this flow reversal occurs after only a few seconds in that the sample gas quickly reaches the main columns 16. FIG. 4 illustrates this reverse flow condition. In particular, this figure illustrates a standby mode of the pneumatic system 88. As indicated in FIG. 4, the flow of carrier gas is reversed by toggling the valve 104 such that the carrier gas supplied by the first branch line 92 is diverted away from the inlet supply line 28 to the purge supply line 98. Accordingly, the relatively high volume supply of carrier gas to the inlet 12 is terminated and instead provided to the purge supply line 98. The carrier gas travels through this purge supply line 98 to each of the purge lines 82–86. As indicated in FIG. 4, the flows are restricted by flow restricters 114–118 provided along each of the purge lines 82–86. These flow restricters 114–118 prevent pneumatic cross-talk across the various purge lines 82–86.

In an alternative arrangement (not shown), the pneumatic system can be simplified to connect the system supply line 90 directly to the inlet supply line 28 and the purge supply line 98. In such an arrangement, each of the inlet supply lines 28 and the purge supply line 98 can comprise its own flow controller to control flow through the lines. As will be appreciated by persons having ordinary skill in the art, this arrangement would simplify the pneumatics, in that branch lines 92, 94, and 96 would be unnecessary, yet would provide the same functionality as the system 88 shown in FIG. 3.

After passing through the flow restricters 114–118, the carrier gas travels to each of the column supply lines 56–60. As is apparent from FIG. 4, the pneumatic system 88 of the chromatograph 10 is balanced such that the flows provided from the purge lines 82–86 are divided so that roughly half of the flow provided to each chromatograph level or channel travels through the pre-columns 14 while the other half flows through the main columns 16. Operating in this manner, the flow through the main columns 16 is uninterrupted upon switching from the first mode illustrated in FIG. 3 to the second mode illustrated in FIG. 4.

As is further identified in FIG. 4, the carrier gas travels through the pre-columns 14, back through the pre-column supply lines 36–40, to the splitter 34. From the splitter 34, the carrier gas is delivered to the inlet 12. Once there, the carrier gas is purged from the chromatograph 10. In particular, the second inlet vent 32 is used to clear the main body of the inlet of the analytes. To similarly prevent contamination of the septum 26, the flow of gas supplied by the second branch line 94 purges the septum through the first vent line 30.

As is apparent from the above, the reverse flow of the carrier gas purges the first half of the gas chromatograph 10 of sample analytes. However, as is known in the art, heavier sample analytes will be retained by the stationary phase disposed on the inner surfaces of the pre-columns 14. Although these analytes will elute from the stationary phase with time, the duration of this time will vary depending upon the temperature at which the pre-column is maintained. In the first pre-column 42, for instance, which is maintained at a relatively high temperature, the relatively light analytes of the sample will be quickly eluted from the stationary phase and therefore will be relatively quickly removed from the gas chromatograph 10 during stand-by operation (if they have not already been removed previously). The heavier analytes, however, will be retained in the pre-column 42 for a longer period of time. Accordingly, the reverse flow of carrier gas through the third pre-column 46 will not necessarily remove the heavier analytes from the pre-columns 14 until a substantial passage of time. Therefore, where multiple sample analyses are conducted in succession, the lower pre-columns, such as pre-columns 44 and 46, may comprise a build-up of these heavier analytes. However, in that the gas chromatograph 10 operates in the stand-by mode the great majority of the time during chromatograph use, the analytes are constantly driven back through the system such that these analytes will not reach the main columns 16 and will eventually be purged from the chromatograph.

In the main columns 16, the analytes are exposed to varying degrees of heat across the several chromatographs layers. As is known in the art, this heat causes the analytes to elute from the stationary phase so that they can be carried by the carrier gas to the detectors 18. In the example described above, where the first main column 50 is at approximately 300° C., the second main column 52 is at approximately 200° C., and the third main column 54 is at approximately 100° C., the relatively light analytes will quickly pass through the first and second main columns 50 and 52 due to their elevated temperatures. Therefore, the first and second detectors 70 and 72 normally will quickly detect these analytes.

Figure 5:
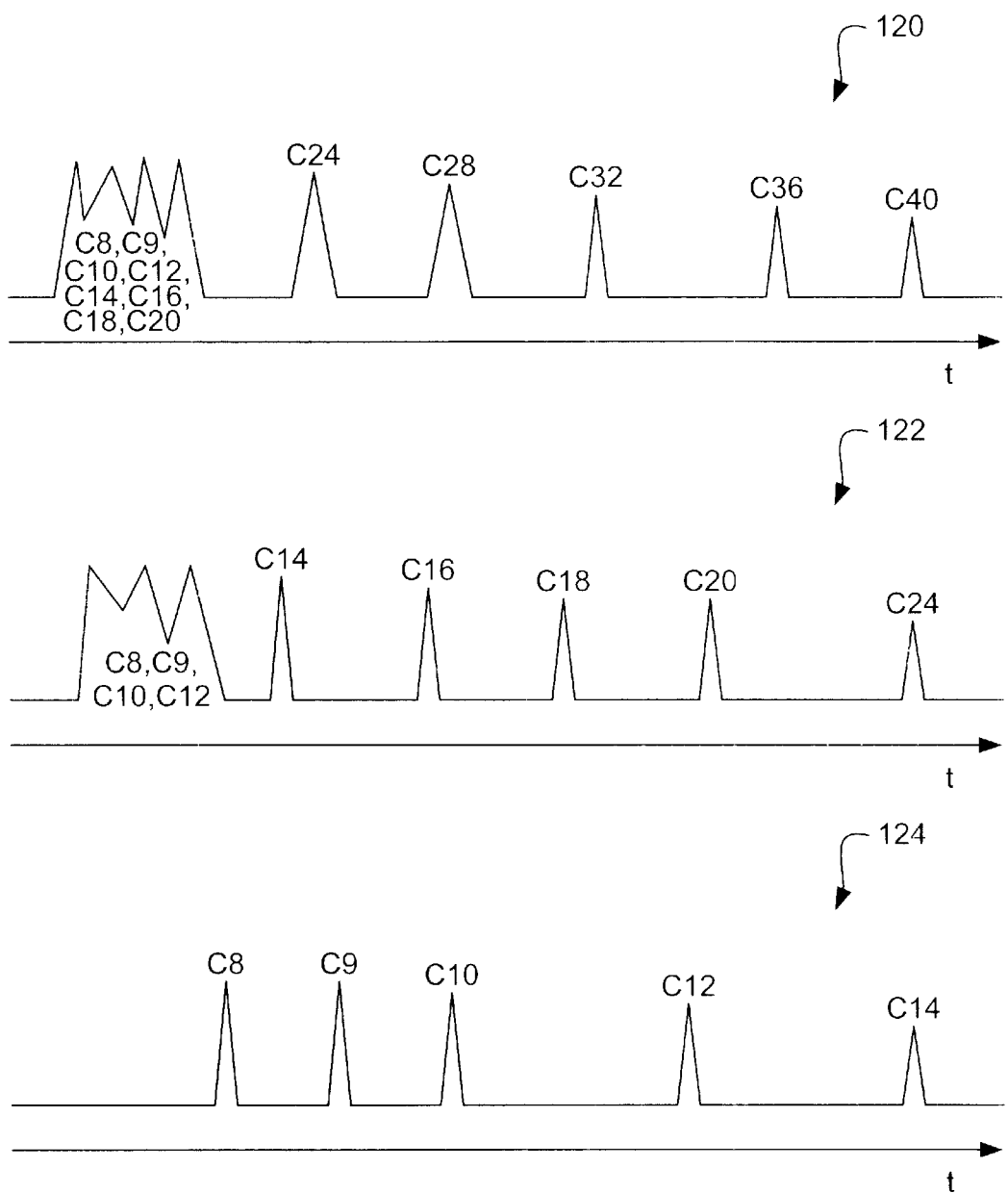
FIG. 5 is a schematic of various chromatogram channels output from the gas chromatograph of FIGS. 1 and 2.

FIG. 5 illustrates various chromatograms of the various detectors 70–74. These chromatograms can be designated as first, second, and third channels 120, 122, 124, respectively, which pertain to the first, second, and third detectors 70, 72, and 74, respectively. As indicated in FIG. 5, the first and second channels 120 and 122 comprise a plurality of peaks representing the relatively light analytes at the beginning of the chromatograms. As identified in these chromatograms, these relatively light analytes are bunched together and therefore not adequately separated for detection by a universal detector. However, due to the temperature gradient across the various chromatograph layers, these lighter analytes will be adequately separated, and therefore detected, in the lower temperature layers. For instance, the third channel 124 may contain each of these relatively light analytes with good separation. In the example shown in FIG. 5, the analytes detected with the third detector 74 comprise C8, C9, C10, C12, and C14.

As is further indicated in FIG. 5, the second detector 72 can detect each analyte that is heavier than the heaviest analyte detected by the third detector 74. Accordingly, the second channel 122 can comprise peaks for C14, C16, C18, C20, and C24. In similar manner, the first detector 70 can detect each analyte heavier than the heaviest analyte detected by the second detector 72. Accordingly, by way of example, the first channel 120 can comprise peaks for C24, C28, C32, C36, and C40. Normally, it is desirable to have peak overlap across any two adjacent channels. This permits the channels to be calibrated against each other in terms of channel gains. This calibration can be used to account for different split ratios across the layers, if any.

As will be appreciated by persons having ordinary skill in the art, the separation of these various analytes across the various chromatograph layers expedites the detection process in that the first layer can be used to detect the heaviest analytes, the third layer can be used to detect the lightest analytes, and the second layer can be used to detect the in-between analytes. Therefore, every sample analyte can be detected substantially simultaneously in a short period of time with adequate analyte separation. By way of example, the chromatograms illustrated in FIG. 5 can be generated in approximately 100 seconds. Moreover, in that separate layers are provided at separate temperatures, there is no need to ramp the temperature of the chromatograph up from an initial to a peak temperature. Accordingly, no cool down time between analysis cycles is necessary.

As identified above, the retention of heavier analytes in the lower layers of the chromatograph 10 normally will not skew the results of the sample analysis. However, from time to time it may be desirable to purge the system under relatively hot conditions after repeated use of the chromatograph 10 to ensure that the heavier compounds are removed. By way of example, the chromatograph 10 can be operated with both the first and second heat sources 22 and 24 at a temperature of approximately 350° C. and the system operating in the stand-by mode shown in FIG. 4. After the expiration of a predetermined amount of time operating at this temperature, for example 15 to 30 minutes, the chromatograph 10 typically will be completely purged of all sample analytes.

Figure 6:
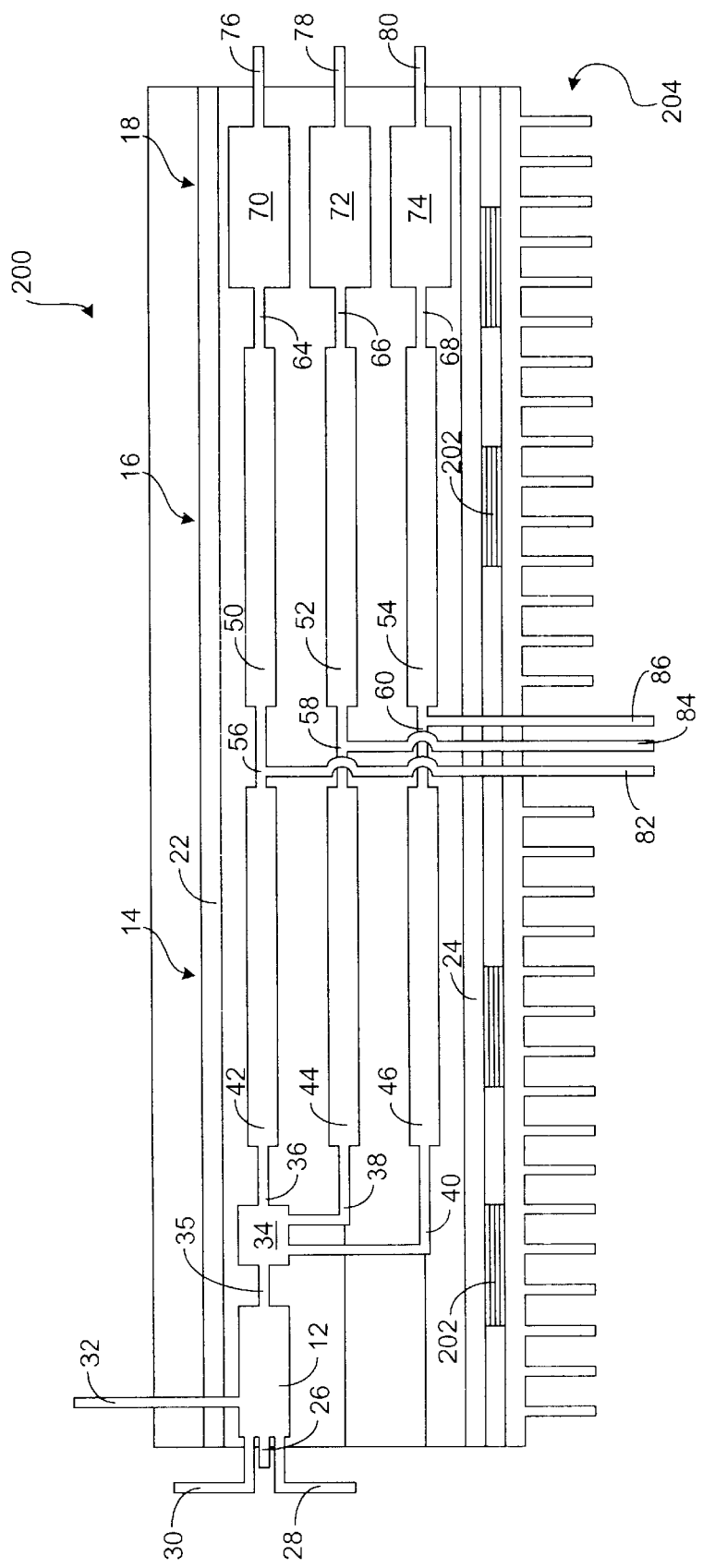
FIG. 6 is a schematic side view of a second gas chromatograph of the present invention.

FIG. 6 illustrates a second gas chromatograph 200 of the present invention. As is apparent from this figure, the chromatograph 200 shares many of the components of the gas chromatograph 10 described above with reference to FIGS. 1–5. Accordingly, the discussion of the second gas chromatograph 200 is limited to the features that are not provided in the gas chromatograph 10. Similar to the gas chromatograph 10, the gas chromatograph 200 includes a first heat source 22 and a second heat source 24. However, in the embodiment shown in FIG. 6, the gas chromatograph 200 is intended for sub-ambient (i.e., low temperature) use. For instance, the chromatograph 200 can be used to analyze refrigerant materials. As known in the art, the analytes of such materials elute from stationary phases at relatively low temperatures. Accordingly, the first heat source 22 can be maintained at a temperature of approximately 250° C. and the second heat source 24 is maintained at a temperature of approximately 0° C. With these temperatures, the various layers can be maintained at temperatures of approximately 200° C., 100° C., and 0° C., respectively.

To maintain the second heat source 24 at a low temperature, the gas chromatograph 200 normally further comprises one or more thermoelectric coolers 202 that are positioned directly adjacent the second heat source. By way of example, each thermoelectric cooler 202 can comprise a plurality of diode junctions (not shown) arranged in parallel that develop a heat gradient when current is applied across the junctions. In the arrangement shown in FIG. 5, for instance, the coolers 202 can be operated to remove heat from the second heat source 24 so that this heat can be removed by a heat sink 204. In addition to the features of this arrangement shown in FIG. 5, cryogenic cooling can also be used, if desired.

Figure 7:
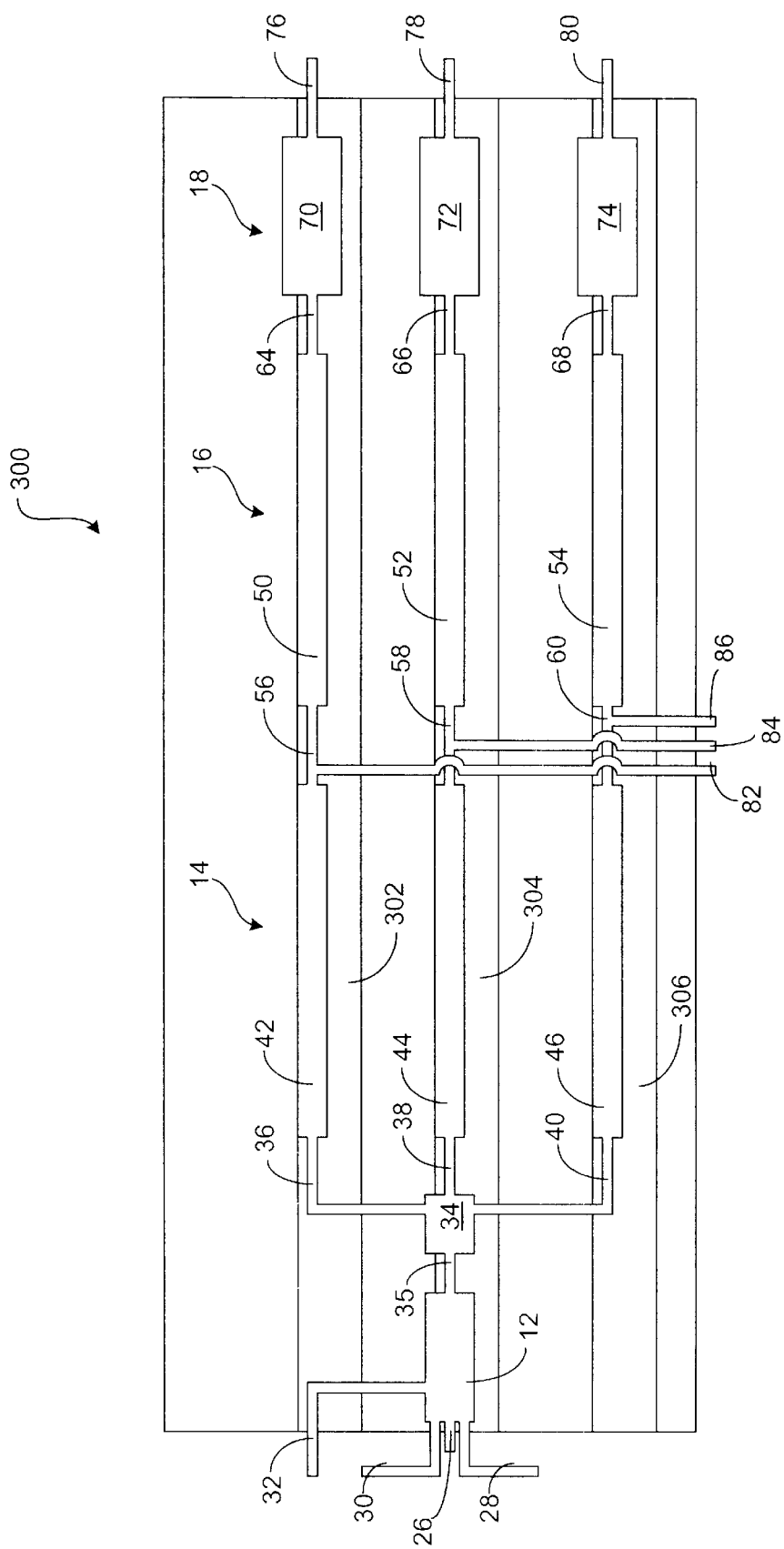
FIG. 7 is a schematic side view of a third gas chromatograph of the present invention.

FIG. 7 illustrates a third gas chromatograph 300 of the present invention. As is apparent from this figure, the chromatograph 300 again shares many of the components of the gas chromatograph 10 described above with reference to FIGS. 1–5. Accordingly, the discussion of the third gas chromatograph 300 is again limited to the features that are not provided in the gas chromatograph 10. As is apparent from FIG. 7, the gas chromatograph 300, like the chromatograph 10, includes three separate layers along which carrier gas can be directed. However, in the embodiment shown in FIG. 7, three heat sources 302, 304, and 306 are provided that individually heat each of the three respective chromatograph layers. In particular, each layer (i.e., pre-column 14 and main column 16) is placed in direct contact with a heat source 302–306. With this arrangement, the chromatograph layers (and therefore their temperatures) are less sensitive to changes in their physical positions. As known in the art, temperature changes can occur due to column temperature change. Therefore, with the various pre-columns 14 and main columns 16 in direct contact with the heat sources 302–306, the chromatograph 300 is not susceptible to such temperature variations, thereby yielding more accurate analysis results. In use, the heat sources 302–306 can be heated such that the second heat source 304 has the greatest temperature to optimize the thermal design. In particular, such a heating arrangement conserves energy in that substantially all the heat generated by the hottest heat source is utilized. Preferably, the heat source temperatures and insulation layer thicknesses are designed so that the thermal power conducted into each heat source is less than the thermal power conducted out of the heat source. In an alternative arrangement (not shown), the heat sources 302, 304, and 306 can be divided to separately heat the inlet, pre-columns, and main columns.

Figure 8:
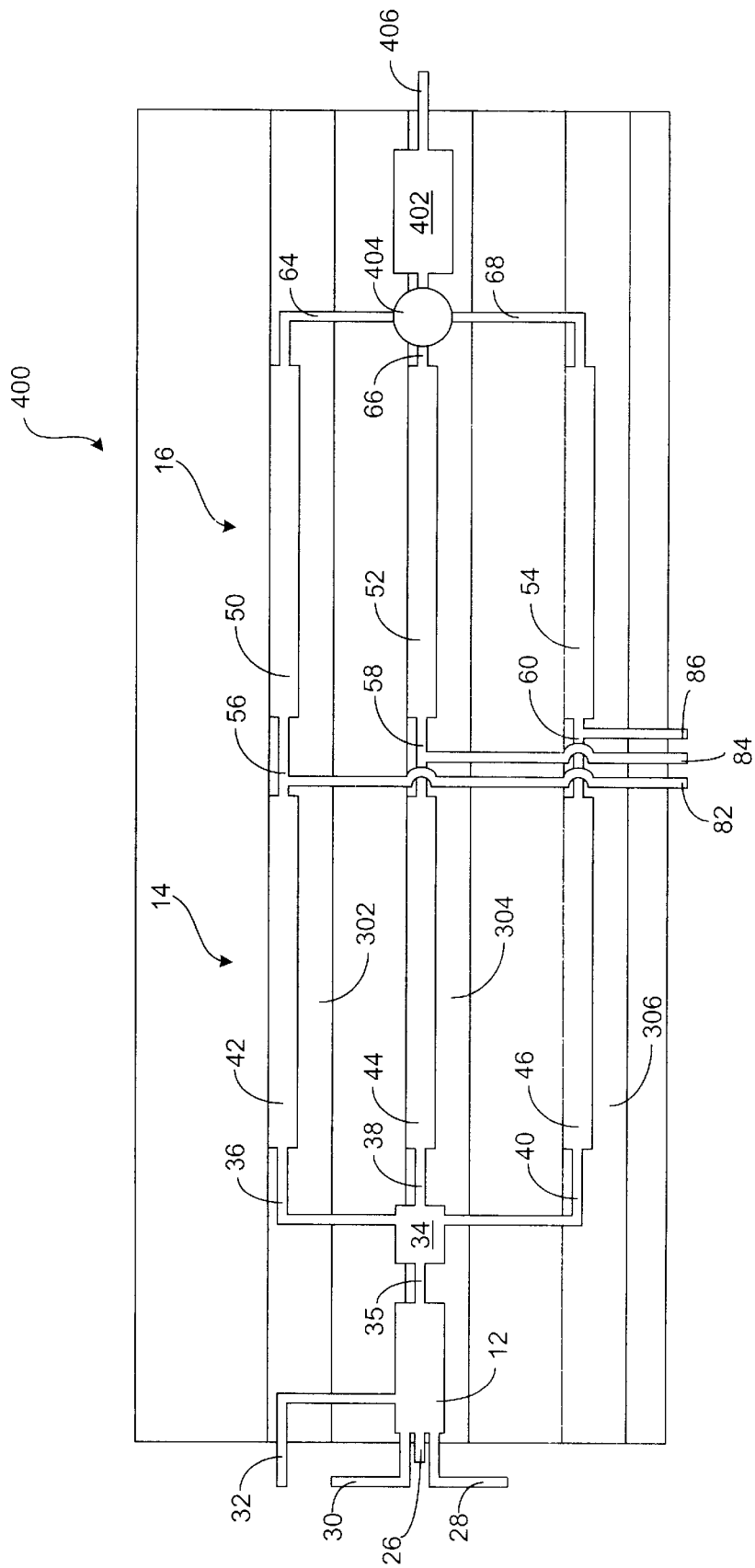
FIG. 8 is a schematic side view of a fourth gas chromatograph of the present invention.

FIG. 8 illustrates a fourth gas chromatograph 400 of the present invention which is substantially identical to the gas chromatograph 300 shown in FIG. 7 except for the provision of a single detector 402, for instance a universal detector. As indicated in FIG. 8, each of the detector supply lines 64–68 of the various chromatograph layers meet at a junction 404 that leads to the detector 402. As is further identified in FIG. 8, the detector 402 includes its own vent line 406. The embodiment shown in FIG. 8 is used in similar manner to that shown in FIG. 7. However, the gas chromatograph 400 is specifically intended for use with relatively simple sample materials. In particular, the chromatograph is well-suited for sample materials that have fewer analytes such that there is adequate peak separation to distinguish and identify the various sample analytes. Where the single detector 402 is a selective detector such as a mass spectrometer, the gas chromatograph 400 can also be used with complex samples and over-lapping peaks can be resolved using known deconvolution algorithms.

While particular embodiments of the invention have been disclosed in detail in the foregoing description and drawings for purposes of example, it will be understood by those skilled in the art that variations and modifications thereof can be made without departing from the scope of the invention as set forth in the following claims. For instance, although particular embodiments having particular numbers of chromatograph layers have been illustrated and described, it is to be appreciated that alternative arrangements are feasible. In addition, although the detectors have been illustrated as forming a part of the chromatograph, persons having ordinary skill in the art will understand that the detector(s) could be external to the chromatograph. Such a detector could, by way of example, comprise a universal detector or selective detector. Furthermore, although gas chromatographs are described herein, it will be understood that the concepts disclosed herein, such as multiple layers and multiple columns, apply to other technologies.

What is claimed is:

1. A gas chromatograph, comprising:
    an inlet that receives a sample to be analyzed;
    multiple columns each receiving a portion of the sample, each column comprising:
        a pre-column in fluid communication with the inlet, the pre-column having a stationary phase coating its inner surfaces;
        a main column in fluid communication with and downstream from the pre-column, the main column having a stationary phase coating its inner surfaces;
    a detector in fluid communication with and downstream from the main columns; and
    a purge line that is in direct fluid communication with each pre-column and each main column, the purge line being configured to supply a reverse flow of carrier gas to each pre-column and a forward flow of carrier gas to each main column.

2. The chromatograph of claim 1, further comprising a pneumatic system in fluid communication with the inlet and the purge line, the pneumatic system being configured to selectively deliver carrier gas to the inlet and the purge line.

3. The chromatograph of claim 1, wherein the chromatograph comprises multiple layers, each layer comprising a column of the multiple columns.

4. The chromatograph of claim 3, further comprising a splitter in fluid communication with the inlet and each pre-column, the splitter being configured to divide a flow of carrier gas supplied by the inlet to supply each of the pre-columns with carrier gas.

5. The chromatograph of claim 3, further comprising first and second heat sources, the heat sources being arranged such that each of the layers is disposed between the heat sources so that where the heat sources are maintained at separate temperatures, a thermal gradient develops across the chromatograph layers.

6. The chromatograph of claim 3, further comprising one detector in separate fluid communication with each of the main columns.

7. The chromatograph of claim 3, wherein each of the main columns is in fluid communication with the detector.

8. The chromatograph of claim 3, further comprising a plurality of coolers and a heat sink that remove heat from the pre-column and main column of one of the chromatograph layers.

9. The chromatograph of claim 1, further comprising a heat source in direct contact with each pre-column and each main column.

10. A gas chromatograph for analyzing a sample, the chromatograph comprising:

means for receiving the sample;

multiple layers, each layer comprising:

first means for processing the sample in fluid communication with the means for receiving the sample, the first means for processing having a stationary phase coating;

second means for processing the sample in column in fluid communication with and downstream from the first means for processing, the second means for processing having a stationary phase coating;

means for detecting analytes of the sample in fluid communication with and downstream from the second means for processing the sample; and purge means for supplying a reverse flow of carrier gas to each of the first means for processing the sample and a forward flow of carrier gas to each of the second means for processing the sample.

11. The chromatograph of claim 10, further comprising means for delivering carrier gas to the means for receiving the sample.

12. The chromatograph of claim 10, further comprising means for dividing a flow of carrier gas supplied by the means for receiving to each of the first means for processing of each layer.

13. The chromatograph of claim 10, further comprising first and second means for heating the chromatograph that are arranged such that each of the layers is maintained at separate temperatures so that a thermal gradient develops across the chromatograph layers.

14. The chromatograph of claim 10, further comprising means for removing heat from the first and second means for processing of one of the chromatograph layers.

15. A gas chromatograph having a plurality of layers, the chromatograph comprising:

an inlet that receives a sample to be analyzed;

a column disposed in each of the plurality of chromatograph layers, each column being in fluid communication with and downstream from the inlet and comprising:

a pre-column in fluid communication with the inlet, the pre-column having a stationary phase coating its inner surfaces; and a main column in fluid communication with and downstream from the pre-column, the main column having a stationary phase coating its inner surfaces;

a splitter in substantially direct fluid communication with the inlet and each column, the splitter being configured to divide a flow of carrier gas from the inlet to each of the columns;

a detector in substantially direct fluid communication with and downstream from the columns; and a plurality of purge lines, each purge line being in direct fluid communication with a pre-column and main column of a chromatograph layer.

16. The chromatograph of claim 15, further comprising a pneumatic system in fluid communication with the inlet, the pneumatic system being configured to deliver carrier gas to the inlet.

17. The chromatograph of claim 15, further comprising first and second heat sources, the heat sources being arranged such that each of the layers is disposed between the heat sources so that where the heat sources are maintained at separate temperatures, a thermal gradient will develop across the chromatograph layers.

18. The chromatograph of claim 15, further comprising one detector in separate fluid communication with each of the columns.

19. The chromatograph of claim 15, wherein each of the columns is in fluid communication with the detector.

20. The chromatograph of claim 15, further comprising a plurality of coolers and a heat sink that remove heat from the column of one of the chromatograph layers.

21. The chromatograph of claim 15, wherein the purge lines are configured to supply reverse flows of carrier gas to the pre-columns and forward flows of carrier gas to the main columns.

22. A method for analyzing a sample material with a gas chromatograph, comprising:

carrying the sample in gas form through multiple pre-columns of the gas chromatograph with a carrier gas;

permitting the sample gas to reach multiple main columns in direct fluid communication with and downstream from the multiple pre-columns, wherein each of the multiple pre-columns and multiple main columns are arranged in separate layers;

reversing the flow of carrier gas through the multiple pre-columns while simultaneously maintaining forward flow of carrier gas through the multiple main columns; and detecting the analytes of the sample material with one or more detectors in fluid communication with and downstream from the multiple main columns.

23. The method of claim 22, further comprising heating the gas chromatograph such that at least two of the chromatograph layers are at different temperatures.

24. The method of claim 22, further comprising separately detecting sample analytes from each column.

25. The method of claim 24, further comprising producing a separate chromatogram channel for each column.

26. The method of claim 23, wherein heating comprises developing a thermal gradient across the chromatograph so that each layer is maintained at a different temperature.

* * * * *